United States Patent [19]

Inagi et al.

[11] Patent Number: 4,525,347

[45] Date of Patent: * Jun. 25, 1985

[54] ANTIINFLAMMATORY ANALGESIC GELLED OINTMENT

[75] Inventors: Toshio Inagi, Hachioji; Toyojiro Muramatsu, Sayama; Hidetaka Nagai, Hachioji, all of Japan

[73] Assignee: Kowa Company Limited, Nagoya, Japan

[ * ] Notice: The portion of the term of this patent subsequent to Jan. 5, 1999 has been disclaimed.

[21] Appl. No.: 468,491

[22] Filed: Feb. 22, 1983

Related U.S. Application Data

[63] Continuation-in-part of Ser. No. 304,909, Sep. 23, 1981, abandoned, which is a continuation of Ser. No. 87,574, Oct. 23, 1979, Pat. No. 4,309,414, which is a continuation of Ser. No. 918,021, Jun. 22, 1978, abandoned.

[51] Int. Cl.$^3$ .................. A61K 31/40; A61K 31/78
[52] U.S. Cl. ........................... 424/81; 424/78; 514/420
[58] Field of Search .............. 424/81, 274, 362, 365

[56] References Cited

U.S. PATENT DOCUMENTS 3,629,412  12/1971  Silber et al. ................. 424/232
4,126,681  11/1978  Reller ........................ 424/234
4,244,942  1/1981   Kamishita et al. .............. 428/81

Primary Examiner—Leonard Schenkman
Attorney, Agent, or Firm—Oblon, Fisher, Spivak, McClelland & Maier

[57] ABSTRACT

An antiinflammatory analgesic ointment comprising: (a) an antiinflammatory amount of indomethacin; (b) a medium consisting of a hydroxy compound in the range of from 15 to 85% by weight, water in the range of 30 to 55% by weight and a gelating agent being present in an amount sufficient to effect gelation of said ointment and selected from the group consisting of a cellulose compound and a carboxyvinyl polymer which has been neutralized with aqueous ammonia or an amine; (c) an adjuvant being present in the range of from 0.5 to 5% by weight and selected from the group consisting of a $C_1$-$C_5$ alcohol ester of a $C_4$-$C_{14}$ monocarboxylic acid and a $C_1$-$C_3$ alcohol diester of a $C_4$-$C_{10}$ dicarboxylic acid; and (d) water in an amount sufficient to make up the balance of the ointment, said ointment being adjusted in its pH from an acidic to slightly basic level sufficient to solubilize said indomethacin in the composition but not too basic a pH level to cause decomposition of said indomethacin.

2 Claims, No Drawings

ANTIINFLAMMATORY ANALGESIC GELLED OINTMENT

CROSS REFERENCE TO RELATED APPLICATION

This is a continuation-in-part of application Ser. No. 304,909 filed Sept. 23, 1981 now abandoned, which is a continuation of application Ser. No. 87,574 filed Oct. 23, 1979 (now U.S. Pat. No. 4,309,414), which was a continuation application of application Ser. No. 918,021 filed June 22, 1978 (now abandoned).

BACKGROUND OF THE INVENTION

1. Field of the Invention

This invention relates to an antiinflammatory analgesic ointment containing indomethacin as an active component.

2. Description of the Prior Art

Indomethacin is represented by the formula,

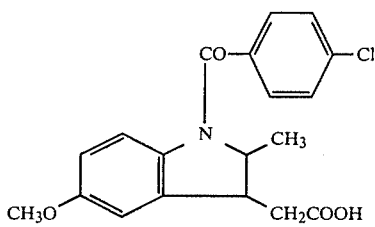

and is a known non-steroidal compound which possesses excellent antiinflammatory activity.

Indomethacin was marketed in Japan in 1966 and has been widely used in capsule form for the treatment of chronic articular rheumatism, arthritis deformans, inflammatory diseases and inflammations which occur after operations. Indomethacin is a very effective antiinflammatory drug, and in fact, its effects are deemed to be the greatest among currently used nonsteroidal antiinflammatory agents.

However, the administration of indomethacin induces adverse effects within the human body such as gastroenteric disorders resulting from the oral use of the drug.

In order to overcome the difficulties of the oral administration, suppositories have been developed and employed in plastic surgery and other fields for the alleviation of inflammation, pain and fever in a patient to be treated. The adverse reactions such as gastroenteric disorders from the oral use of indomethacin are somewhat decreased by the administration of the drug in suppository form. It is impossible however to administer indomethacin even in suppository form to any patient suffering from peptic ulcer since the administration of indomethacin in suppository form would result in decreased appetite, nausea, vomiting, stomach ache, diarrhea and loose passage. There is therefore a continuing need for the development of an improved mode of administration of indomethacin.

The present inventors have found upon extensive study that indomethacin, when administered topically, exhibits antiinflammatory analgesic activity to the same extent as attained by its internal use and that the adverse reactions attributable to the administration of indomethacin are completely eliminated.

However, indomethacin ointments cannot be produced by conventional methods of preparing ointments because indomethacin is only slightly soluble in water and common media. For topical use, indomethacin suspended in conventional ointment bases is observed to remain unabsorbed by the skin of human beings and does not exhibit any therapeutic effect.

In order to produce an ointment in which indomethacin is dissolved and which can be easily absorbed into the skin of human beings, the present inventors have conducted continuous research, and as a result, have discovered that indomethacin which is dissolvable in a medium consisting of glycol, an alcohol and water and which is gellable with a gelling agent can be administered topically without accompanying adverse side-effects which are experienced with the conventional forms of administration and that the absorption of indomethacin by the skin is substantially increased by combination with an adjuvant.

SUMMARY OF THE INVENTION

Accordingly, it is an object of the present invention to provide an antiinflammatory analgesic ointment which is devoid of the difficulties of the existing forms of administration of indomethacin and which is very stable and effectively useful for topical administration.

Briefly, this object and other objects of the present invention as hereinafter will become more readily apparent can be attained in an antiinflammatory analgesic ointment, comprising: (a) an antiinflammatory amount of indomethacin; (b) a medium consisting of a hydroxy compound in the range of from 15 to 85% by weight, water in the range of 30 to 55% by weight and a gelating agent being present in an amount sufficient to effect gelation of said ointment and selected from the group consisting of a cellulose compound and a carboxyvinyl polymer which has been neutralized with aqueous ammonia or an amine; (c) an adjuvant being present in the range of from 0.5 to 5% by weight and selected from the group consisting of a $C_1$-$C_5$ alcohol ester of a $C_4$-$C_{14}$ monocarboxylic acid and a $C_1$-$C_3$ alcohol diester of a $C_4$-$C_{10}$ dicarboxylic acid; and (d) water in an amount sufficient to make up the balance of the ointment, said ointment being adjusted in its pH from an acidic to slightly basic level sufficient to solublize said indomethacin in the composition but not too basic a pH level to cause decomposition of said indomethacin.

DETAILED DESCRIPTION OF THE PREFERRED EMBODIMENTS

Suitable hydroxy compounds useful in the invention include glycols such as propylene glycol, butylene glycol, polyethylene glycol and the like, and alcohols such as ethanol, isopropanol and the like. The hydroxy component of the present composition may be any hydroxy compound used alone or in combination with another hydroxy compound. When a combination is used, a preferred combination is glycol in an amount of 5 to 35% with any selected alcohol in the range of 10 to 50%. Particularly preferred is the combination range of 15 to 85% of hydroxy compound and 30 to 55% of water.

(All percentages used herein are on a weight basis unless otherwise specifically indicated.)

Suitable gelating agents useful in the invention include a carboxyvinyl polymer, a cellulose compound and the like. Suitable cellulose compounds include hydroxyethyl cellulose, methyl cellulose, carboxymethyl cellulose, hydroxypropyl cellulose, hydroxypropylmethyl cellulose and the like.

The carboxyvinyl polymer previously neutralized with aqueous ammonia or an organic amine such as diisopropanol amine or triethanolamine is used as a gelating agent. This gelating agent is preferably present such that the concentration is 0.5 to 5%.

Suitable adjuvants useful in the invention include a $C_1-C_5$ alcohol ester of $C_4-C_{14}$ monocarboxylic acid and a $C_1-C_3$ alcohol diester of $C_4-C_{10}$ dicarboxylic acid such as diisopropyl adipate, diethyl sebacate, ethyl caproate, ethyl laurate and the like. Any one selected adjuvant is preferably added in a concentration of 0.5 to 5%. Indomethacin is expected to exhibit a substantial therapeutic effect when utilized in an amount over the range of 0.5 to 1.5%.

The final pH of the ointment according to the invention should be adjusted from 4.8 to 7.5, preferably from 6.2 to 7.2. A pH level below 4.8 would induce crystallization of indomethacin during the ointment preparation. A pH level above 7.5 would result in decomposed indomethacin and hence in unstability and would adversely affect the human body.

The ointment of the invention can be produced by (1) swelling a gelating agent in water, (2) dissolving indomethacin and an adjuvant in a mixture of a glycol and an alcohol and (3) adding (2) to (1), and further adding an amine to the resulting mixture to form a desired gel ointment.

The ointment thus prepared can be stored in a stable state for a long period of time and hence exerts therapeutically excellent, antiinflammatory analgesic effects when applied to the human body by coating, as will be herinafter described.

The above disclosure generally describes the present invention. A more complete understanding will be obtained by the following specific examples which are presented for purposes of illustration only and are not construed as limiting to the invention.

EXAMPLE 1

| 1 Carboxyvinyl polymer | 1.0 g |
|---|---|
| 2 Indomethacin | 1.0 g |
| 3 Propylene glycol | 10.0 g |
| 4 Ethanol | 40.0 g |
| 5 Diisopropanolamine | 1.1 g |
| 6 Purified water | An amount sufficient to bring the final weight to 100 g |

(A) Swell (1) in 20 g of (6).
(B) Dissolve (2) in a mixture of (3) and (4).
(C) Add (B) and (A) and mix until the mixture is completely hydrated.
(D) Dissolve (5) in 10 g of (6). Add the mixture to (C) with mixing. Bring the resultant mixture to the final weight with the remainder of (6) and stir the composition until it becomes homogeneous.

EXAMPLE 2

| 1 Carboxyvinyl polymer | 1.0 g |
|---|---|
| 2 Indomethacin | 1.0 g |
| 3 Propylene glycol | 20.0 g |
| 4 Ethanol | 30.0 g |
| 5 Diisopropanolamine | 1.0 g |
| 6 Purified water | An amount sufficient to bring the final weight to 100 g |

(A) Swell (1) in 20 g of (6).
(B) Dissolve (2) in a mixture of (3) and (4).
(C) Add (B) to (A) and mix until the mixture is completely hydrated.
(D) Dissolve (5) in 10 g of (6). Add the mixture to (C) with mixing. Bring the resultant mixture to the final weight with the remainder of (6) and stir the composition until it becomes homogeneous.

EXAMPLE 3

| 1 Carboxyvinyl polymer | 1.0 g |
|---|---|
| 2 Indomethacin | 1.0 g |
| 3 Propylene glycol | 12.0 g |
| 4 Ethanol | 30.0 g |
| 5 Diisopropyl adipate | 2.0 g |
| 6 Diisopropanolamine | 1.1 g |
| 7 Purified water | An amount sufficient to bring the final weight to 100 g |

(A) Swell (1) in 20 g of (7).
(B) Dissolve (2) in a mixture of (3), (4) and (5).
(C) Add (B) to (A) and mix until the mixture is completely hydrated.
(D) Dissolve (6) in 10 g of (7). Add the mixture to (C) with mixing. Bring the resultant mixture to the final weight with the remainder of (7) and stir the composition until it becomes homogeneous.

EXAMPLE 4

| 1 Carboxyvinyl polymer | 1.0 g |
|---|---|
| 2 Hydroxyethyl cellulose | 1.0 g |
| 3 Indomethacin | 1.0 g |
| 4 Polyethylene glycol 300 | 10.0 g |
| 5 Ethanol | 30.0 g |
| 6 Diisopropyl adipate | 2.0 g |
| 7 Diisopropanolamine | 0.9 g |
| 8 Purified water | An amount sufficient to bring the final weight to 100 g |

(A) Swell (1) and (2) in 20 g of (8).
(B) Dissolve (3) in a mixture of (4), (5) and (6).
(C) Add (B) to (A) and mix until the mixture is completely hydrated.
(D) Dissolve (7) in 10 g of (8). Add the mixture to (C) with mixing. Bring the resultant mixture to the final weight with the remainder of (8) and stir the composition until it becomes homogeneous.

EXAMPLE 5

| 1 Hydroxypropyl cellulose | 5.0 g |
|---|---|
| 2 Indomethacin | 0.5 g |
| 3 Propylene glycol | 20.0 g |
| 4 Triethanol amine | 0.35 g |
| 5 Ethanol | 30.0 g |
| 6 Purified water | An amount sufficient to bring the final weight to 100 g |

(A) Swell (1) in 20 g of (6).
(B) Dissolve (2) in a mixture of (3) and (5).
(C) Dissolve (4) in the remainder of (6).

(D) Add (A) and (C) to (B) and stir the resultant mixture until it becomes homogeneous.

EXAMPLE 6

Inhibitory Effect on Carrageenan-Induced Edema:

Wister male rats each weighing about 200 g, each group consisting of six rats, were subcutaneously administered 0.05 ml of a 1% carrageenan solution on their hind right paws. Immediately thereafter, about 100 mg of the ointment prepared in Example 1 was coated over each injected area. Each coating was covered with a polyethylene film, which was fixed with gauze. Two hours later, both the polyethylene film and the gauze were removed. One hour after removal, the weight of edema was measured. The control group was coated only by the ointment base and thereafter treated in the same manner as in the test groups. The results are as shown in Table 1.

TABLE 1

| Test ointment | Weight of edema (g) Mean ± error | Inhibition ratio (%) |
|---|---|---|
| Control | 0.50 ± 0.03 | — |
| Indomethacin ointment (1%) | 0.35 ± 0.04 | 31.1* |

*$p < 0.05$

EXAMPLE 7

Inhibitory Effect on Acceleration of Blood Vessel Permeability:

Guinea pigs were coated twice with about 50 mg of the ointment prepared as in Example 1 on their hair-removed back skins at an interval of one hour. One hour after a second coating, a 1% Evans Blue solution was injected intravenously. Immediately thereafter, 10 μg of a histamine hydrochloride solution was intradermally injected into each ointment-coated region. Thirty minutes later, the animals were depleted to death. Each skin dyed in blue was exfoliated, and the pigment was extracted with pyridine. The control group was coated only by the ointment base and thereafter treated in the same manner as in the test groups.

The results obtained are as shown in Table 2.

TABLE 2

| Test ointment | Evans' Blue (μg/region) Mean ± error | Inhibition ratio (%) |
|---|---|---|
| Control | 246.2 ± 26.5 | — |
| Indomethacin ointment (%) | 202.8 ± 28.1 | 17.6 |

EXAMPLE 8

Absorption from Skin:

Guinea pigs were coated with about 1 g of each of the ointments prepared as described in Examples 1 and 3 and suspended with about 0.1 g of the ointment on the back skins each having a region of 2×2 cm from which the hair was removed one day after hair cutting. Five hours after coating, the preparation was recovered, and the absorption ratio was calculated from the amount recovered. The results obtained are as shown in Table 3.

TABLE 3

| | Test ointment | | |
|---|---|---|---|
| Absorption ratio | Cream* | Ointment in Example 1 | Ointment in Example 3 |
| After 5 hours (%) | 6.0 ± 2.0 | 13.4 ± 2.6 | 25.5 ± 1.1 |

*Prepared according to the method reported in Europ. J. Pharmacol., 3, 157 (1968)

EXAMPLE 9

The results obtained for the clinical studies of 84 cases conducted by three establishments are as shown in Table 4 in which parenthesized are the percentage values.

TABLE 4

| | Excellent | Good | Fair | Ineffective | Aggravation | Unknown | Total |
|---|---|---|---|---|---|---|---|
| Distorsion | 1 | 8 | 2 | 2 | 0 | 0 | 13 |
| Contusion | 0 | 7 | 0 | 2 | 0 | 0 | 9 |
| Fracture, dislocation and sequelae | 0 | 2 | 4 | 1 | 0 | 0 | 7 |
| Traumatic arthritis | 0 | 1 | 2 | 1 | 0 | 0 | 4 |
| Total | 1 | 18 | 8 | 6 | 0 | 0 | 33 |
| | (3.0) | (54.5) | (24.2) | (18.2) | | | |
| Arthritis deformans | 0 | 3 | 10 | 4 | 0 | 0 | 17 |
| Myositis | 0 | 2 | 0 | 1 | 0 | 0 | 3 |
| Total | 0 | 10 | 19 | 12 | 0 | 1 | 42 |
| | | (23.8) | (45.2) | (28.6) | | (2.4) | |
| Swelling post operative | 0 | 3 | 2 | 1 | 0 | 0 | 6 |
| Others | 1 | 0 | 1 | 1 | 0 | 0 | 3 |
| Sum total | 2 | 31 | 30 | 20 | 0 | 1 | 84 |
| | (2.4) | (36.9) | (35.7) | (23.8) | | (1.2) | |

EXAMPLE 10

| | | |
|---|---|---|
| 1 | Carbopol 940 (The B. F. Goodrich Company) | 1.0 g |
| 2 | Indomethacin | 0.7 g |
| 3 | Propylene glycol | 8.0 g |
| 4 | Ethanol | 40.0 g |
| 5 | Aqueous ammonia 10% | 0.6 g |
| 6 | Distilled water | An amount sufficient to bring the final weight to 100 g |

(A) Dissolve (2) in (3) and (4).
(B) Disperse (1) in (A).
(C) Add (6) to (B) and swell the resultant mixture.
(D) Add (5) to (C) and stir the composition until it becomes homogeneous.

EXAMPLE 11

| 1 Indomethacin | 1.0 g |
|---|---|
| 2 Isopropyl alcohol | 45.0 g |
| 3 Hydroxypropylmethyl cellulose | 1.5 g |
| 4 Triethanolamine | 0.4 g |
| 5 Distilled water | An amount sufficient to bring the final weight to 100 g |

(A) Dissolve (1) in (2).
(B) Swell (3) in 40 g of (5).
(C) Add (B) to (A). Add the remainder of (5) and (4) to (C) and stir the composition until it becomes homogeneous.

This invention now being fully described, it is apparent to those skilled in the art that many changes and modifications can be made to the invention without departing from the spirit or scope of the invention set forth herein.

What is claimed is:

1. An anti-inflammatory analgesic gelled ointment, comprising:
   (a) indomethacin in the range of 0.5 to 1.5% by weight;
   (b) a medium ranging from 15 to 85% by weight and consisting essentially of a hydroxy compound selected from the group consisting of propylene glycol, butylene glycol, polyethylene glycol, ethanol, and isopropanol, water in the range of 30 to 55% by weight, and a gelating agent ranging from 0.5 to 5% by weight of a carboxyvinyl polymer which has been neutralized with aqueous ammonia;
   (c) an adjuvant being present in the range of 0.5 to 5% by weight and selected from the group consisting of a $C_1$-$C_5$ alcohol ester of a $C_4$-$C_{14}$ monocarboxylic acid and a $C_1$-$C_3$ alcohol diester of a $C_4$-$C_{10}$ dicarboxylic acid; and
   (d) water in an amount sufficient to make up the balance of said ointment, said ointment being adjusted in its pH of 4.8 to 7.5.

2. An anti-inflammatory analgesic gelled ointment, comprising:
   (a) indomethacin in the range of 0.5 to 1.5% by weight;
   (b) a medium ranging from 15 to 85% by weight and consisting essentially of a hydroxy compound selected from the group consisting of propylene glycol, butylene glycol, polyethylene glycol, ethanol, and isopropanol, water in the range of 30 to 55% by weight, and a gelating agent ranging from 0.5 to 5% by weight and selected from the group consisting of a cellulose compound and a carboxyvinyl polymer which has been neutralized with aqueous ammonia;
   (c) an adjuvant being present in the range of 0.5 to 5% by weight and selected from the group consisting of a $C_1$-$C_5$ alcohol ester of a $C_4$-$C_{14}$ monocarboxylic acid and a $C_1$-$C_3$ alcohol diester of a $C_4$-$C_{10}$ dicarboxylic acid; and
   (d) water in an amount sufficient to make up the balance of said ointment, said ointment being adjusted in its pH of 4.8 to 7.5.

* * * * *